US008787555B2

(12) United States Patent
Gonen et al.

(10) Patent No.: US 8,787,555 B2
(45) Date of Patent: Jul. 22, 2014

(54) PROCESS FOR OBTAINING EXPERT ADVICE ON-DEMAND

(75) Inventors: Shlomo Gonen, Calabasas, CA (US); Jonathan A. Gonen, Calabasas, CA (US); David Gonen, Calabasas, CA (US); Darren Berkovitz, Bell Canyon, CA (US); Stacy Stubblefield, Los Angeles, CA (US); Micah Grossman, Westlake Village, CA (US); Jordan Michaels, Westlake Village, CA (US)

(73) Assignee: Telethrive, Inc., Westlake Village, CA (US)

(*) Notice: Subject to any disclaimer, the term of this patent is extended or adjusted under 35 U.S.C. 154(b) by 945 days.

(21) Appl. No.: 11/958,855

(22) Filed: Dec. 18, 2007

(65) Prior Publication Data

US 2008/0147741 A1  Jun. 19, 2008

Related U.S. Application Data

(60) Provisional application No. 60/870,692, filed on Dec. 19, 2006.

(51) Int. Cl.
*H04M 3/523* (2006.01)
*G06Q 50/00* (2012.01)

(52) U.S. Cl.
USPC ............ 379/265.11; 379/265.12; 379/265.13; 705/2; 705/3; 705/346

(58) Field of Classification Search
USPC ............... 379/114.02, 265.11–265.14; 705/3, 705/346, 2; 709/206
See application file for complete search history.

(56) References Cited

U.S. PATENT DOCUMENTS

| 5,509,064 | A  | * | 4/1996  | Welner et al. ............ 379/265.02 |
| 7,076,037 | B1 | * | 7/2006  | Gonen et al. ............. 379/114.02 |
| 7,120,647 | B2 | * | 10/2006 | Venkatesh et al. .............. 706/60 |
| 7,787,609 | B1 | * | 8/2010  | Flockhart et al. ......... 379/265.01 |
| 2001/0032244 | A1 | * | 10/2001 | Neustel .......................... 709/206 |
| 2006/0229918 | A1 | * | 10/2006 | Fotsch et al. ...................... 705/3 |

* cited by examiner

*Primary Examiner* — Harry S Hong
(74) *Attorney, Agent, or Firm* — Kelly & Kelley, LLP

(57) ABSTRACT

Obtaining expert advice on-demand includes maintaining a substantially real-time list of available experts in selected fields, in an electronic database. The system receives a request from a customer for expert advice in one or more of the selected fields maintained in the electronic database. The system then electronically identifies one or more available experts to the customer in response to the request received and routes the request for expert advice to at least one of the available experts.

18 Claims, 5 Drawing Sheets

PROCESS FOR OBTAINING EXPERT ADVICE ON-DEMAND

BACKGROUND OF THE INVENTION

The present invention generally relates to communication systems. More particularly, the present invention relates to a process for obtaining expert advice and/or communicating with others in real-time via an on-demand communication network.

Historically, the primary means for communicating in real-time was via a land-line telephone through a Public Switch Telephone Network (PSTN). The PSTN is a public circuit-switched telephone network for routing telephone calls. For example, one person dials the phone number of a second person. The PSTN processes the dialed telephone number and routes the caller to the receiver to create a voice communication connection between the two parties. In some instances, there were per minute charges for the telephone call, such as with 1-900 numbers. More recently, the real-time communication options have greatly expanded beyond the traditional land-line telephones. For example, voice communication connections are frequently made via traditional land-line telephones, cellular telephones, satellite telephones, Voice over Internet Protocol (VoIP) connections, video conference phone connections or satellite voice/data connections. New channels of communication are ever increasing beyond the traditional PSTN. These channels increase the flexibility and the type of communication between communicating parties. Most importantly, the development of such new technology presents new service and business opportunities for entities capable of providing expert advice or otherwise endeavoring to communicate with others in ways previously impossible.

More specifically, the medical field is an industry greatly dependent upon communication between contracting parties. Health care traditionally required patients to physically see a doctor at a local medical facility. The costs of seeing a health care profession is expensive. It is well known that health care costs, especially in the United States, have significantly increased over the last few decades. Additionally, more workers are without health care insurance to pay for the ever increasing health care costs. As a result, the private health care industry has endeavored to develop alternative health care solutions that increase consumer convenience while driving down costs for consumers, physicians, employers, and insurance companies. Increasing the ease and flexibility of communication between health care facilities and patients is one area to reduce the costs of health care while creating new business opportunities for the economy.

Private health care industry companies are now using the growth in communication options between health care professionals and patients to employ new means of providing health care. New health care solutions include technologically advanced telephone communication solutions, streamlined walk-in clinics, and "cash friendly" medical practices. Specifically, companies such as TelaDoc and Dial-A-Doc use advances in voice communication and data transmission technology as a means for interconnecting medical professionals with patients. For instance, TelaDoc is a professional association that contracts with licensed physicians capable of providing the necessary medical care to patients. Patients contact TelaDoc and register with the service by providing relevant medical history information. Patients call a toll-free TelaDoc number to request a consultation with a health care professional when the patient is in need of medical care or needs medical advice. TeleDoc processes the request after the patient hangs up the telephone. The patient waits for a return phone call. Ideally, the patient receives a callback from a physician within three hours. The licensed physician returning the patient phone call provides the level of needed health care advice such as recommending a diagnosis or treatment. The patient may be billed for each diagnosis, phone call, etc. The physician may be contracted with TeleDoc to receive a flat payment for each returned phone call or a per minute rate, depending on the contracted arrangement with the service.

While the existing telephone consultation companies have certain advantages of potentially providing lower cost health care to patients, such consultation companies do have several drawbacks. One particular drawback is that patients must wait for a return call from the physician. This can be particularly frustrating in a society that seeks immediate diagnosis for ailments. Often, it takes thirty to forty minutes for TeleDoc to process the patient request, find an available physician, and thereafter have the physician contact the patient. Sometimes it takes up to three hours to connect a physician and patient in real-time communication. Of course, the patient may otherwise be unavailable when the physician finally calls the patient back. Ailments progress and proliferate when left untreated until a later stage in development. Limited educational resources also increase the difficulty for patients to obtain the information necessary to identify or even treat an ailment. Moreover, existing telephone consultation services are particularly disadvantageous for patients seeking immediate medical information regarding a particularly distressing or critical medical condition. Accordingly, such patients may opt to visit the emergency room a local hospital instead of waiting for the return phone call.

Moreover, the severity and complexity of ailments increase when left untreated.

Therefore, there is a need in the art for a process for obtaining expert advice on-demand utilizing the advances in communication technology. Specifically, such a system should include methods for connecting a caller with a corresponding expert, should allow the expert to set availability, should allow the expert to set a fee schedule, and should be available to callers via a broad range of communication networks. The present invention fulfills these needs and provides further related advantages.

SUMMARY OF THE INVENTION

The process for obtaining expert advice on-demand in accordance with the present invention includes maintaining a substantially real-time list of available experts in selected fields, in an electronic database. The system receives a request from a customer for expert advice in one or more of the selected fields maintained in the electronic database. The customer may enter a username/password, an account number, or a voucher number to directly access the system to contact an expert. The system of the present invention then electronically identifies one or more available experts to the customer in response to the request received. The customer may receive advertisements from the system prior to being routed to the expert. Thereafter, the system routes the request for expert advice to at least one of the available experts, thereby establishing a communication link between the customer and the selected expert over an electronic communication network. Preferably, the customer is routed to an available expert selected by the customer. Subsequently, the customer may be rerouted to a new expert on the list as selected by the customer, by a computer, by the first selected expert, or randomly.

The system of the present invention also creates accounts for customers and experts in the electronic database. The customers may be immediately associated with those accounts by being identified via caller identification, Automatic Number Identification, or other data input by the customer upon calling the system. Customer specific account information is stored in individual customer accounts. Access to those accounts may be restricted to authorized persons such as the expert and the customer. In one embodiment of the present invention, the authorized expert is a medical expert, and the customer specific information includes medical records. Each expert may also be assigned a unique identification number or individually identifiable username/password. The identification number or username may be used by the customer to immediately request a specific expert.

The list of available experts may be organized by a ranking system. In one embodiment of the present invention, the system sorts the list of available experts by rating. An expert rating may be at least partially based on data from a customer that rates the expert at the conclusion of a consultation session. Accordingly, the customer is routed to the highest rated available expert in the selected field. The customer may then be rerouted to the next highest rated expert when the highest rated expert does not respond to or rejects the request for expert advice. In another embodiment, the system ranks the list of available experts from the lowest bidding available expert to the highest available bidding expert. Accordingly, the customer is routed to the lowest available bidding expert in the selected field.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
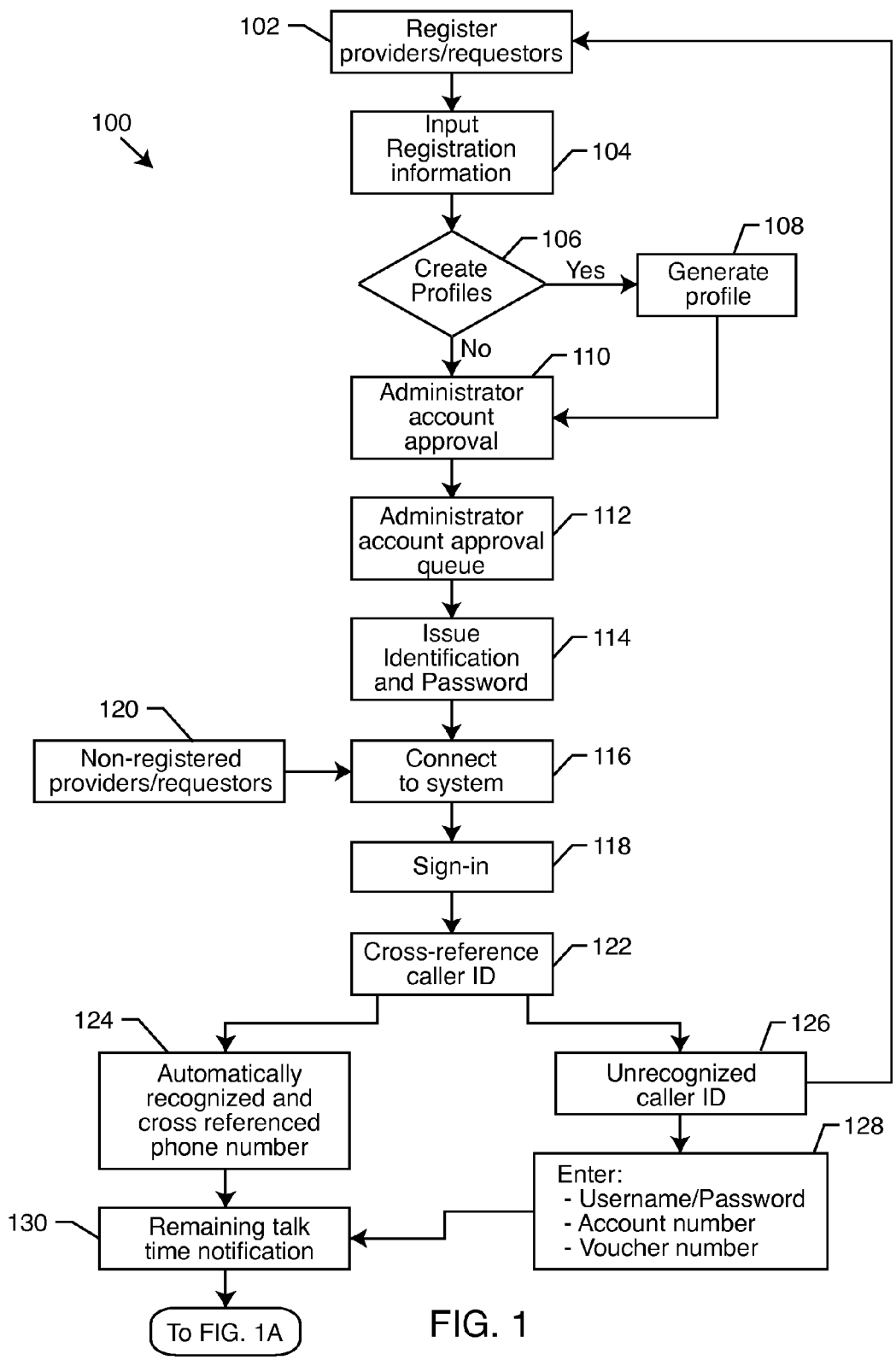
FIG. 1 is a flowchart illustrating the steps for obtaining expert advice on-demand, in accordance with the present invention.
Figure 1A:
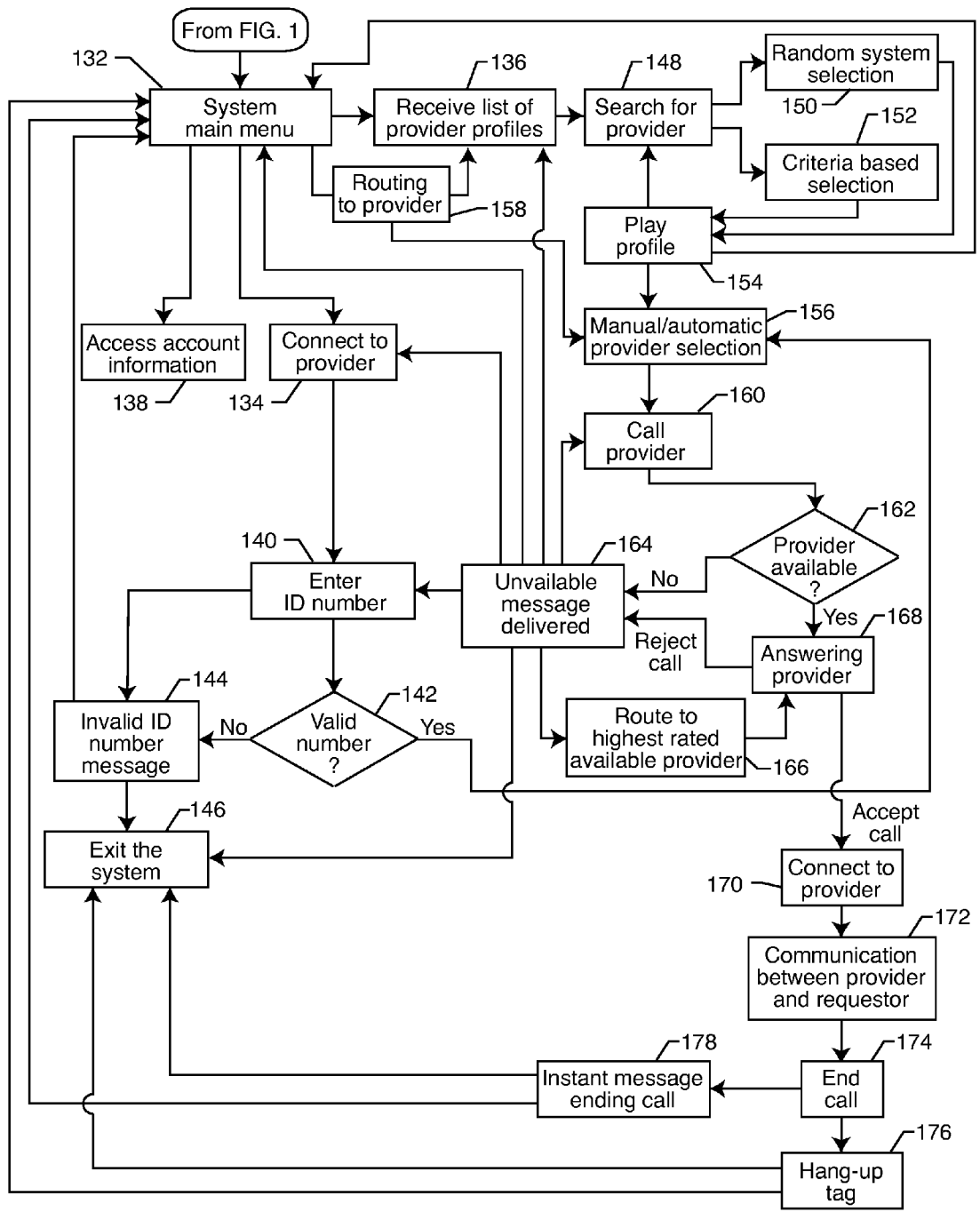
FIG. 1A is a continuation of the flowchart of FIG. 1.

As shown in the drawings for purposes of illustration, the present invention for a process for obtaining expert advice on-demand is generally referenced by the reference number (100). As shown in FIGS. 1-1A, the process for obtaining expert advice on-demand (100) is capable of placing one or more entities in real-time contact via a broad range of communication networks. The present invention is especially useful in providing a communication network for connecting the general public with health care professionals (specifically physicians) and celebrities.

In accordance with the general process for obtaining expert advice on-demand (100) shown in FIGS. 1-1A, a providing party ("provider") is any entity that provides information to a requesting party ("requester"). The provider is referenced as a "physician" with respect to on-demand medical services embodied in FIGS. 2-2A and as a "celebrity" with respect to on-demand celebrity services embodied in FIG. 3. The provider may convey a wide range of information that includes expertise, advice, information, consulting, entertainment, companionship, guidance, translation, therapy, medical advice, how-to information, etc. The provider may be a person, business, government agency, or other electronically based service such as Interactive Voice Response (IVR) telephony technology. An IVR system can respond to voice-activated commands with pre-recorded or dynamically generated audio communication to direct system callers through a series of menus. IVR allows callers to interact with a database via a touch-tone phone. An IVR system can be used to enter information into a database and later retrieve the information from the database for disclosure to an expert or other professional in accordance with the present invention. Typically, IVR technology does not require human interaction over the telephone and may limit access rights to certain information in the database. IVR may be particularly useful in the storage and retrieval of sensitive medical information as only a physician and corresponding patient would have access to such information. There may be different IVR menu languages based on the language or country where the call originates.

As briefly described above, the requesting party, or requestor, is any party seeking information from the provider. The requestor may include a person, group, company, government agency, or any other entity seeking information. The requestor is specifically referenced as a "patient" with respect to on-demand medical services embodied in FIGS. 2-2A and as a "caller" with respect to on-demand celebrity services embodied in FIG. 3. A connection between the requester and the provider is made through a land-line telephone, internet-base telephone or data communications connection, satellite-based voice or data connection, email, or any combination of the foregoing. Any mechanical or electrical device capable of relaying voice or data information between two entities in real-time is a preferable communication network usable to connect the provider and the requester in accordance with the present invention.

As referenced herein, a "communication network" provides a connection between the provider and the requester by any method known in the art wherein the provider and requester can exchange information between one another. Such a communication network may include real-time live (or near-live) transmission of voice or data communication such as electronic messages (email, internet chat, text messages, SMS messages) compressed or uncompressed video and audio transmissions, etc. via audio, visual or data networks such as PSTN, VoIP ("rated number" or "prepaid account"), and satellite-based networks. Devices usable with such a communication network include land-line telephones, cellular phones, VoIP phones (e.g. Skype telephone and video services via the Internet), and satellite-based phones. As more fully described below, these communication networks are used to transfer data to and from information databases accessible by authorized entities (e.g. physician and patient). Information may be added or removed from the databases via the internet (on-line forms and data entry), personal computer (speech recognition software or keyboard/mouse), or IVR (over-the-phone speech recognition). Any information stored in the databases may be changed remotely via any communication network through the data transfer methods described above.

In general, the process for obtaining expert advice on-demand (100) is the ability to connect providers with requestors throughout the world. The aforementioned communication networks enable entities from all over the world to communicate with one another in real-time. There are currently no systems in place to take advantage of such communication networks capable of connecting providers and requesters. Therefore, the present invention uses communications networks to enable entities to contact one another to exchange information regarding specific interests. Advantageously, participating entities may originate from various backgrounds, cultures, nationalities, etc. Specifically, the present invention provides a process for connecting requesters with providers in order to obtain expert advice on-demand.

The first step in the process for obtaining expert advice on-demand (100) is to register a provider with the system (102). The provider (or authorized representative) inputs information (104) regarding the provider into a system database during registration. Input information should specifically include the price or rate that the provider will charge per time increment connected to each requestor (e.g. $5.00 per minute). The provider also inputs contact information such as name, address and telephone number, preferable payment information (e.g. check or direct deposit), availability to receive phone calls, contacting telephone number (subject to verification), alert information (e.g. mobile phone number, text messaging number, or email address), languages spoken, geographic location, expertise, experience, profession, etc.

The system also provides the capability for the provider to create a profile (106). The profile allows requestors to view personal information regarding the provider. Requestors may therefore make better informed decisions when selecting a provider from whom to obtain expert advice on-demand. Preferably, the profile includes information regarding the provider such as age, gender, birthday, interests, personality traits, and other interests or professional accolades. The provider may manually generate the profile (108) or allow the system to automatically generate the profile (108). Profiles may include bold text, color text, pictures, and other personal information that convey the interests and expertise of the provider. An alternative name or nickname may be displayed in association with the profile instead of a legal name. The provider contact information and corresponding profile must be submitted for administrator approval (110) before being posted publicly. Like providers, requestors may also register with the system via the same or similar processes as described above. The same or similar processes for the requestors include inputting at least contact information such as name, address and telephone number, including geographic location.

Profiles submitted for approval are placed in an administrator account queue (112) in the order received. Administrators can view the queue, send messages to providers or requesters to change inputted information, and accept or reject the profiles. Moreover, edits to accepted accounts may need to be reviewed again for approval before the changes are publicly posted. Account edits requiring approval may include profile or picture information. The account and profile review approval process ensures that profile content meets certain base requirements set by the system administrator (e.g. prohibit profanity or other vulgar). Accordingly, the system issues the provider or the requestor an identification name and password (114) after registration and profile creation is complete and accepted.

Once approved, providers and requesters must connect to the system (116) before being able to sign-in (118) to their account. Accounts are accessible via telephone, IVR, and preferably the Internet. Provider accounts provide access to identification information, current billing rates (including rate fees and flat fees), availability status, contact availability, contacting telephone number, profile and greeting. The account may also display information accounting for time "worked" within a specific billing period (e.g. monthly), pay statements, yearly earnings, scheduled payments, and a list of answered and unanswered calls by call period (e.g. hourly, daily, weekly, monthly, quarterly, etc.). The provider may also view and edit any of the detailed account and profile information described above. Current ratings and important notices are also posted to each provider account. Access to tech support documents, including tech support tickets, user guides and tutorials are also available through the provider account. Administrators are responsible for responding to support tickets submitted by providers or requesters.

Administrators generally manage the system and facilitate connection between providers and requesters. Administrators have a wide range of responsibilities and access privileges to ensure efficient operation of the system. Moreover, system administrators are responsible for safeguarding account information (e.g. medical records) from unauthorized access. Administrators are generally responsible for the financial operation of the system, which may include approving payments to providers, monitoring payments from requesters, tracking non-call purchases, viewing provider or requestor statements (e.g. monthly bills or payment statements) and adjusting provider pay rates. The system can also compile call statistics that the administrator may monitor to effectuate efficient operation of the system. Such call statistics may include IVR menu selections, missed and rejected calls, call length, call type (e.g. IVR, Internet-based, land-line based, etc.), call frequency, calls by time period (e.g. hour, day, month, etc.) and quantity of requester calls. Administrators also have access to detailed account information that can be compiled into lists of providers and requesters by phone number, email address, provider or requester alerts, or payment information (e.g. credit card or bank account information). The administrator may basically compile detailed statistics regarding any information processed by the system database.

Administrators also have direct access to provider and requestor accounts and can make changes accordingly. Importantly, administrators can suspend, permanently disable, or adjust access privileges of any provider or requestor accounts. The system tracks account activity, as described above, and administrators can set program defaults to cancel or permanently disable accounts based on delinquent behavior such as regularly missing or rejecting phone calls from requesters. In view of such behavior, the administrator may manually adjust provider ratings or change fee rates based on call duration or call quantity. For example, the administrator may determine that calls lasting one to three minutes are charged $10.00 an hour while calls lasting more than eight minutes may be charged $15.00 per hour, or vice versa. The administrator may also adjust calling rates depending on certain hours of the day. The ratings are preferably flexible such that the system administrator can adjust the effect of each missed or rejected call based on the importance of the missed or rejected call. The system may send providers emails when a certain number of calls are missed or rejected. The system may automatically cancel user accounts when a predetermined number of calls are missed or rejected. Administrators preferably communicate directly with registered providers via some form of written or electronic communication including paper letters or statements, email, text message, instant message, or chats. The administrator may also call or leave voice messages with a provider or requestor via the phone or an on-line account. The administrator may also set up content filters or require approval for messages (e.g. email, text messages, chat room content, etc.) sent through the system.

Access privileges to certain features of the system may be based on tiered subscription rates, depending on the revenue system set up by the administrator. In one embodiment of the present invention, requestors pay for access privileges on a periodic basis (e.g. monthly). Requestor accounts may be set up to enable the system to automatically debit a corresponding on-line payment account or bank account. On-line payment accounts may include Pay Pal, eGold or Neteller. Debits may also be made to cash vouchers such as those offered by uCash. Alternatively, requestors may pay for access to the system via a 900 number or a other special VoIP rated number (e.g. a Skype +99 number) that requires a credit card or pre-paid calling card number. Requestors may monitor account debits through the on-line account and preferably receive periodic (e.g. monthly) electronic or paper statements.

Requestors may additionally register and pay for various access levels. Higher access levels having higher monthly rates may provide more access privileges than lower levels. For example, a free, base level enables requestors to call and talk to providers registered with the system for a limited shortened time frame (e.g. five minutes every day for a week). The requestor may view a list of providers or provider profiles while being prevented from enlarging provider pictures, accessing detailed provider information or otherwise contacting providers via email or chat. A second level may include a paid level one. Paid level one includes all the foregoing access rights of the base level, including the ability to enlarge provider pictures, access detailed information on provider profile pages and exchange information with providers via email or text message. Additionally, the system may include a third level; paid level two. Paid level two includes all the access rights of the base level and paid level one, including the ability to communicate with providers, create personal profiles and watch videos. Accordingly, paid level two would have a higher monthly cost than paid level one. The system of the present invention may include more or less base, pay, or premium levels depending on the features and associated costs for administering the system, corresponding database, and communication network.

In an alternative embodiment of the present invention, sign-in (118) does not require registration (120) with the system to communicate with providers. In this embodiment requesters sign-in (118) by supplying payment information, for billing purposes, or providing a pre-paid voucher number. Payment information is preferably a credit card or other automatic debit card. The requester is billed immediately for any charges incurred by contacting the provider. Alternatively, requesters may purchase vouchers for a certain amount of talk time. Vouchers are similar to calling cards and are good for a certain connection time. Requestors (or providers) may buy gift certificates for friends, purchase items from providers, email provider profiles, receive emails when new providers register, or join any one of a number of mailing lists. Registered requesters can also alternatively purchase additional minutes instead of paying a monthly access fee. Of course, sign-in (118) requires inputting a valid username/password, account number or voucher number to access the system.

Affiliates may be also be used in accordance with the system of the present invention to generate revenue for the system administrator or lower subscription fees for providers and requestors. A robust affiliate system tracks providers and requesters referred by other websites. Specifically, the system should track the quantity of requesters and providers referred and the amount of money each requestor or provider brings in to the system. Each affiliate may receive a percentage of the gross revenue for referred providers or requesters. Affiliates may receive flat payments for each provider and requestor referred. Alternatively, affiliates may receive both a percentage of the gross revenue and a flat payment for each provider or requestor referred.

FIGS. 1-1A illustrate the process for connecting a requestor with a provider in accordance with the process of the present invention. In FIG. 1, requestors first connect to the system (116) by dialing a phone number, a premium Skype number, a VoIP communication number or a satellite communication number via a communication network. During the sign-in (118) phase, the system initially cross-references the originating phone number in the system database (122). Automatically recognized and cross-referenced phone numbers (124) are matched with the corresponding requestor account and no further action is required to sign-in (118) to the system. When no account is matched to the phone number (126), the requestor may enter an account number, username/password, a voucher number (128), or register with the system (102) as a new requester. Requestors that register with the system (102) as a new requestor will later have the same menu options as the registered requestors described below. Alternatively, a group of requesters may register with the system (102) through a parent entity such as an insurance company (e.g. Blue Cross Blue Shield) or corporation (e.g. Costco). The system may analyze or customize the accounts associated with each group of requestors depending on the specific needs of the parent entity.

Requestors using an automatically recognized and cross-referenced phone number (124), entering a registered account number, correct username/password or correct voucher number (128) are immediately notified of their remaining talk time (130). The system allows the requester to purchase additional minutes if no minutes remain on the requester account or the voucher. Requestors are only taken to the system main menu (132) when more than zero minutes remain on the requestor account or the voucher. Accordingly, requestors with minutes remaining on their account or voucher are directed to the system main menu (132). The requester is presented with a menu where the requestor may immediately connect to a provider (134), receive a list of provider profiles (136), or directly access account information (138) (when registered). The requestor may select options by pressing buttons on a touch-tone phone or speaking into the telephone. The requester makes a corresponding selection. For example, the requester may say or press "1" to connect immediately to a provider (134) or say or press "2" to receive a list of provider profiles (136). Moreover, the system may employ a more detailed menu system wherein the requestor may narrow the number of providers with whom the system may connect the requestor. As described below, the menu may include one or more selectable criteria or categories of providers.

In one embodiment of the present invention, the requestor directly enters an identification number (140) to access a particular provider from the main menu. A provider identification number typically includes a series of digits that the system uses to validate the request by the requestor. The system then tries to validate the identification number (142). The system may play a message alerting the requestor when an identification number is invalid (144). The requestor is prompted to re-enter the identification number (140), go back to the main menu (132), or exit the system (146). Entry of a valid identification number calls the provider (160), as described more fully below.

In another embodiment of the present invention, the requestor or system may search for a provider (148) from a received list of provider profiles (136). Preferably, the system searches from a list of currently available providers. Available providers may be randomly selected by the system (150). Alternatively, and more typically, the system selects a provider according to requestor and/or system administrator criteria (152), such as rating. The system may randomly choose a provider when several providers have the same rating. The system then conveys the profile of the provider (154) to the requester. The profiles may be conveyed audibly, visually, or a combination thereof. Accordingly, the requester may continue searching for providers (148) and listening to provider profiles (154) before manually selecting a provider (156) to contact. Provider profile information conveyed to the requestor preferably contains some, if not all, the personal provider information described above. Such information should include demographic, physical, and a personal description of the provider. After listening to the profile (154), the requestor may manually select the provider (156), again search for another provider profile (148), or return to the main menu (132).

Alternatively, the system may use an algorithm to route requestors to providers (158). The system administrator may factor in any of the following criterion when designing a routing algorithm: requestor menu selection, provider service price, provider quality, provider rating, provider availability, languages spoken by the provider, geographic location of the provider as compared to the geographic location of the requestor, expertise or experience of the provider, the age of the provider or the profession of the provider. Of course, the algorithm could factor in any of the personal or professional information entered into the account by the provider. In this embodiment, the system automatically selects the provider (156) via the routing algorithm (158). It is also possible for the system to provide the requestor with an ordered list (136) of providers based on the algorithm. The requestor uses the received list (136) as described above.

In another alternative embodiment of the present invention, a requester may sign-in (118) to a website hosted by the system administrator to access a searchable database of registered providers (148). Such a criteria based selection (152) may include search categories having any information entered into the provider account that the system can organize. Search results preferably list available providers at the top of the list. Providers may alternatively be listed from highest to lowest ranking or from lowest to highest per minute rate. The requester may be presented with the provider profile (154) via the website. The extent of the provider profile information accessible by the requester depends on the access level of the requester, as described above. Generally accessible information should include the provider name, a picture of the provider, a "call me button", provider location, languages spoken by the provider and current availability of the provider. Preferably, the list provides a short caption of each profile. Clicking on a provider profile provides more specific information regarding the provider.

A "call me button" (generally referred herein as "button") enables registered requesters to immediately connect with a provider. Providers may place these buttons anywhere on the Internet, such as networking sites, dating sites, personal home pages, blogs, etc. The buttons may include graphics, HTML code, Java Script, etc. Clicking on a button preferably immediately connects the requestor directly to the provider via a cell phone or other land-line connection. Alternatively, when the provider is unavailable, clicking on the button connects the requestor directly to the system. The button may use any communication network to facilitate the connection between the provider and the requester. Alternatively, the button may allow a requestor to input a phone number therein so the system can bridge the requestor with the provider via the communication network. The connecting phone number may be assigned to the provider by the system or be a phone number initially entered by the provider during registration. Routing via the button also works with extension numbers and usernames/nicknames that can adequately identify and route requesters to the provider. Of course, other connection methods known in the art could be used to automatically connect the provider with the requestor via the "call me button".

Alerts may also be integrated into the system of the present invention. Alerts notify providers of a potential connection with a requestor when the provider is off-line. For example, should a requestor click on the "call me button" or otherwise attempt to contact the provider through the phone or internet, the alert notifies the provider that the requester endeavors to contact the provider. The alert may be an audible message, visual message, text message, or other notification that a requester desires to communicate with the provider.

The system calls the provider (160) once a provider is selected (156). Providers are selected (156) when a requester enters a valid provider identification number (142), a requester selects a provider (156) from a list of providers conveyed by the system, or by the system routing algorithm (158). The system then determines provider availability (162). The requestor receives a provider unavailable message (164) from the system when the provider is unavailable. Unanswered calls are treated as a call to an unavailable provider. The requestor may elect to receive an email or a text message when the desired provider becomes available. Alternatively, the requestor may leave a message and wait for a return call from the provider. The requestor then has several other options. The requester may choose to call the provider (160) again. Here, the system may limit the number of attempts the requester attempts to connect with the provider. Alternatively, the provider may enter a new identification number (140) of another provider. When a provider is unavailable, the system could subsequently convey another provider profile (136) to the requester or automatically route the requester to the next highest rated provider (166). Alternatively, the requestor could return to the main menu (132) or exit the system (146) altogether.

The answering provider (168) has the option to accept or reject the call from the requester. The system treats a rejected call by the provider as an unanswered call or as a call to an unavailable provider. Thereafter, the system conveys the provider unavailable message (164) to the requester and provides the requester with the options discussed in the preceding paragraph. The process is repeated until the requester connects with a provider (170) that accepts the call, there are no more qualified providers, or the requestor exits the system (146).

The answering provider (168) receives a message from the system that a requester is trying to connect to the provider. The system may convey additional information to the provider before the provider decides to accept or reject the contact. Such additional information may include requestor name, the nature of the call, or information requested by the requestor (e.g. medical treatment). The provider accepts or rejects the call using a touch-tone phone or voice activated commands. If the provider accepts the call, a message may be delivered to the provider indicating the duration of the call (e.g. a three-minute, five-minute or unlimited call). Thereafter, the system facilitates the connection between the requester and the provider (170) across any of the previously described communication networks. The bridged provider and requestor then communicate between one another (172). The requester pays for the ensuing connection by any of the methods described herein. Requestor bills may be lowered when an advertising model is incorporated into the system. Alternatively, providers can exchange emails, text messages or on-line chats with requesters.

Oppositely, registered providers may contact registered requesters for the purpose of getting requesters to call the provider or to purchase goods or services from the provider. For example, providers may sell pictures, audio files, videos, ring tones, etc. through the system and in accordance with the present invention.

The system logs the connection details between the provider and requestor to an associated database. Information such as the provider identity, requestor identity (if available), voucher number, call length, call origination number and the type of communication network may all be automatically monitored by the system. Requestor identity is tracked by telephone number, identification number or account number. The system may subsequently end the call (174) by issuing a hang-up tag (176) after expiration of the allowable call session time. Consequently, the provider and requestor are disconnected. The time the call ended is noted in the database. Preferably, the system sends the requestor an instant message (178) to end the call (174). The requestor and provider may exit the system (146) or be directed to the previously described menu system (132) after being disconnected. The requestor is accordingly billed for the time connected to the provider and the provider is credited for the time connected to the requester via any of the debit/payment methods described herein.

Providers receive compensation from the system administrator for connecting to requesters. In one embodiment of the present invention, the provider receives compensation based on a pre-set or provider bid rate for time connected to the requester (i.e. the provider is compensated on a time increment basis). Provider compensation is calculated by multiplying the billing rate (e.g. dollars per minute) by the predetermined time increment (e.g. minutes). For example, a provider having a billing rate of $5.00 per minute would be compensated $50.00 for a ten minute connection with a requester ($5.00/minute multiplied by 10 minutes). In another, more preferable embodiment, the provider receives compensation based on a flat fee charged to the requestor. For example, the provider may receive $30.00 for each requester connection, regardless of the duration of the connection. Alternatively, the rate fees and flat fees may be intermixed according to any algorithm set up by the system administrator. In one example, the requester is charged an initial connection fee and thereafter pays a rate fee having a lower per minute cost than if the requester did not pay the initial connection fee. The system administrator may receive a percentage of the gross income generated by the providers in order to maintain the system. Alternatively, an advertising model may be incorporated into the system to lower the cost of communication for the requester while maintaining the level of compensation for providers. In one embodiment, requesters communicate with providers for free after receiving one or more advertisements.

The system automatically calculates payments owed to providers and automatically bills requesters for corresponding connections. Statements or bills may be generated on a periodic basis (e.g. monthly). Preferably, requester bills are debited directly to a supplied credit card, bank account, calling card account, or a requester account registered with the system and having funds deposited therein. Administrator approval may be required before payments to the providers are automatically generated by the system. After payment approval by the administrator, the system automatically deposits funds into a provider account registered with the system, a supplied credit card or bank account. Of course, the system may automatically generate a paper check that includes payment amount, payee name, and address.

Figure 2:
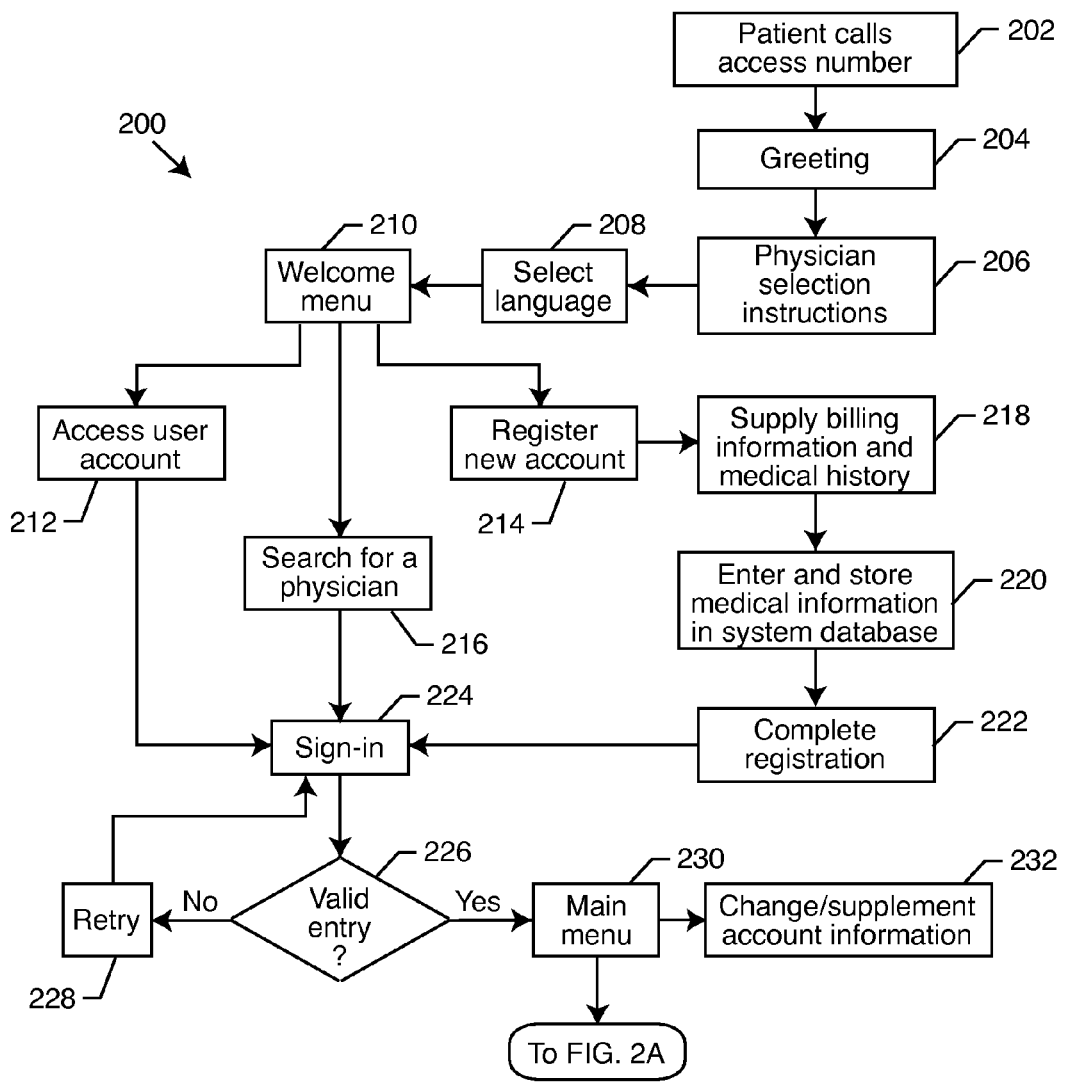
FIG. 2 is a flowchart illustrating the steps of obtaining expert medical advice.
Figure 2A:
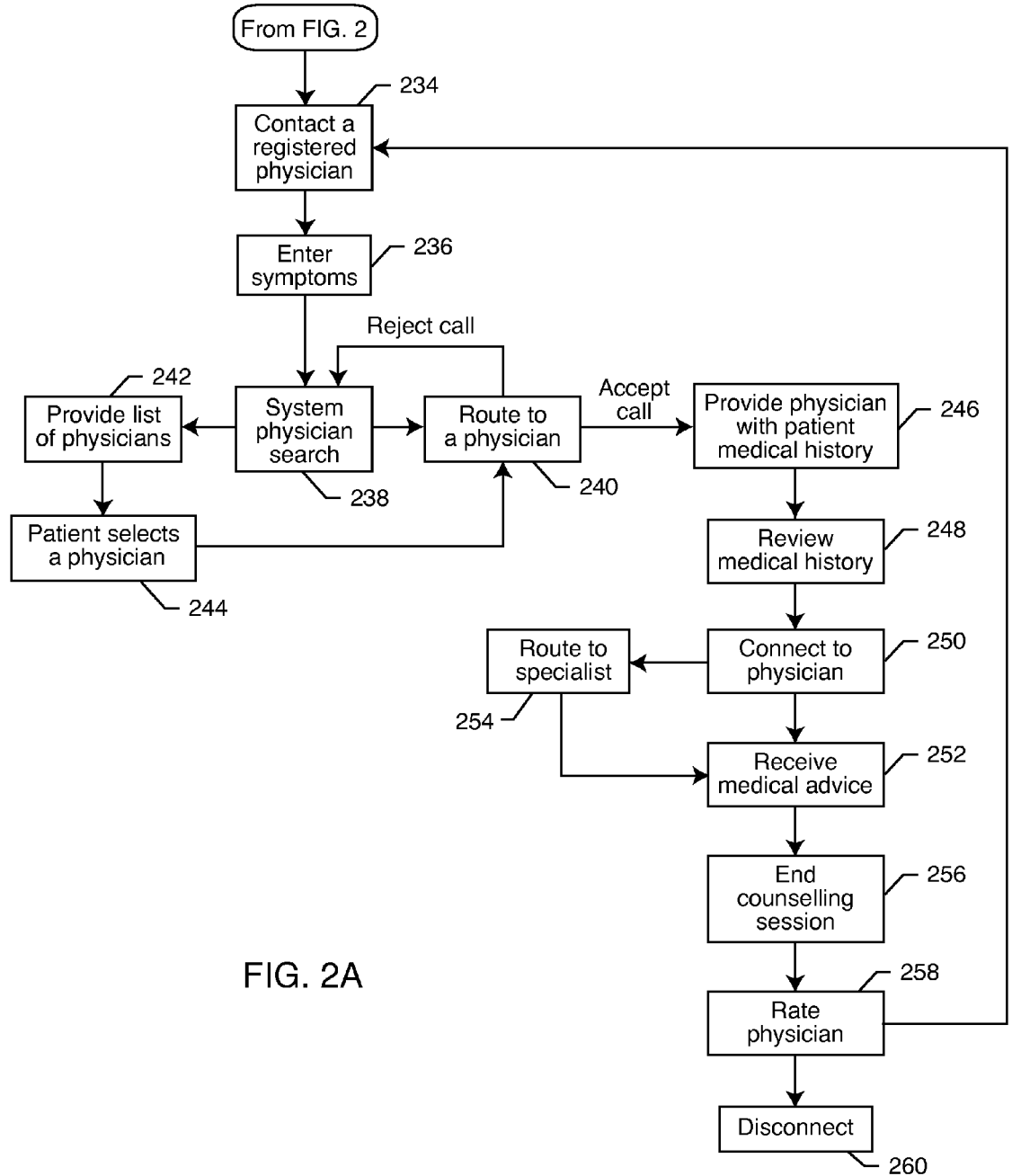
FIG. 2A is a continuation of the flowchart of FIG. 2.

FIGS. 2-2A specifically illustrate the steps in a process for obtaining expert medical advice (200) in accordance with the present invention. A patient calls an access number (202) (e.g. telephone number) to contract the system via any communication network. For example, a patient may dial 1-800-PhoneMD to contact the system. Upon contacting the system, the patient may be presented with a greeting (204) followed by a set of instructions for selecting a physician (206). The patient may be asked to select a language (208) by pressing: "1" for English; "2" for Spanish; etc. Subsequently, the patient receives a set of welcome menu options (210). For example, the menu system might allow registered patients to access the their accounts (212) by pressing or saying "1", while new patients may need to press or say "2" to register a new account (214). Alternatively, existing patients may immediately search for a physician (216) by pressing or saying "3".

New patients must first register with the system (214) and supply the requisite billing information (e.g. credit card, insurance information, etc.), contact information (e.g. name, address, telephone number, etc.), and applicable medical history (e.g. diseases, conditions, allergies, etc.) (218). All applicable account information and medical history information must be recorded and stored in the system database (220) before the patient is connected to a physician.

There are a variety of options available to new patients to complete registration. A customer service representative (e.g. medical office) preferably counsels the new patient and enters applicable medical history information into the system database (220). A medical professional legally licensed to discuss patient medical history may, alternatively, counsel the new patient and enter medical history information into the system database (220) when health care regulations prohibit an unlicensed customer service representative from discussing such information with a new patient. Alternatively, the new patient may enter medical history information directly to the system database (220) via a series of on-line forms on the internet. In an alternative embodiment, the new patient enters medical history information into the system database (220) via the IVR system. Medical history is entered via IVR by the combination of pressing buttons on a touch-tone phone and audibly conveying responses recognizable by voice recognition technology. For example, the new patient may press or say "1" if there is a history of heart disease in the family. Alternatively, the IVR system may record patient responses to questions. Answers to the questions may be reviewed by a medical professional at a later date or simply stored in the system database until needed.

All medical history information is stored securely in the system database. Medical history information is only accessible to authorized persons, such as the patient or consulting physician. The medical history information may be available via the Internet, IVR or other secure communication network. Patient medical information in general may be updated or supplemented in real-time via any of the preceding steps. Alternatively, medical records can be transferred to the system database from a primary care physician or other physician from whom the patient has previously received medical care. With proper authorization, the transferred medical records and any additional consultation information in the patient account may be transferred back to the primary care physician at a later date. This feature enables collaboration and synchronization between the system of the present invention and the primary care physician of the patient. Registration is then complete (222) and the patient receives an account number or username/password.

Registered patients sign-in (224) with the account number or username/password to access the system of the present invention. The system validates the entry (226) and requests the registered patient to retry (228) when the account number or username/password is invalid. The registered patient is connected to the system and a main menu (230) after the correct account number or username/password is entered. The registered patient may change or supplement the account information (232) or choose to connect to a physician (234), shown in FIG. 2A, from the main menu (230).

Physicians must be registered with the system of the present invention before receiving patient contacts. To register, a new physician must fill out an application, including state and Federal licenses, credentials, experience, certifications, a ten-digit contacting telephone number where the physician will receive phone consultation calls, etc. New physicians may register with the system over the phone or the Internet. The application is reviewed manually to ensure proper state and Federal license and certification requirements are met. The physician is subject periodic review to ensure that state and Federal license and certification requirements are continually up-to-date. Once an application is approved, the physician is notified via mail, email, or phone and given system operating instructions.

The registered physician may access account information by telephone, the Internet, IVR or a customer service representative. An account number or username/password is required to access the account information. Alternatively, the system can automatically identify the physician by using Automatic Number Identification (ANI) technology. ANI eliminates the need for the physician to enter an account number or username/password over the phone. Essentially, the telephone number of the physician is used as an identification number. The physician has access to all account information after supplying the necessary sign-in information. The physician may monitor or change active/inactive status and change applicable rate fees, bid amounts or flat fees for receiving a patient contact. For example, the physician may press "1" to change availability from active to inactive. Pressing "1" again changes the status of the physician back to active from inactive. The physician may also change other contact information, such as the contacting telephone number. An electronic message may be sent to the physician indicating completion of any account information updates or changes. An account summary provides the physician with feedback, ratings and a variety of call statistics (e.g. call quantity, call length, call frequency, etc.). The account also allows the physician to schedule available working hours, if the system utilizes a scheduling model. Calls would only be routed to physicians during available working hours.

Registered patients sign-in (224) to the system of the present invention to find a registered physician for treatment. When contacting a physician (234), as illustrated in FIG. 2A, the patient must first enter current symptoms (236) before being connected to a physician. The patient may enter current symptoms (236) by selecting an ailing body part from a list (e.g. press "1" for ears, press "2" for stomach, etc.) or audibly describing the symptoms to a voice recognition system, such as IVR. In one embodiment, the patient automatically receives literature concerning the ailing body part via email, regular mail, text message or any other form of communication described herein. In an alternative embodiment, the patient waits on hold until transferred to a physician. The system may play music or convey advertisements to the patient during this waiting period. Accordingly, the system searches for an available physician (238) and routes the patient to a physician (240) or provides the patient a list of physicians (242) knowledgeable in the type of symptoms described by the patient.

Routing the patient to a physician (240) may be accomplished in a variety of methods. In one embodiment, the system incorporates the processes described in U.S. Pat. No. 7,076,037 to Gonen, et al., the contents of which are herein incorporated by reference. Here, physicians bid against one another to receive patient contacts. A physician that bids $2.00 per minute has a higher call routing priority than a physician that bids $3.00 per minute. Other factors can influence the routing algorithm designed by the system administrator, other than bid amount alone. Factors such as physician specialty, certifications, licenses, association memberships, location as compared to the location of the requestor, and patient ratings are important factors that may be considered. The system should also employ provisions to ensure enough physicians are "active" at any given time to meet patient demand. Thus, physicians may need to be "on call" during unavailable hours so the system can meet increased or unexpected patient demand. Physicians may, alternatively, be allowed to freely change active/inactive status such that there are no set working hours.

The system of the present invention routes the patient to a physician (240) selected by the system or a physician selected by the patient (244) from the provided list of physicians (242). The physician may accept or reject the routed patient call (240). For rejected calls, the system conducts another physician search (238), as described above. When no physicians are currently available to counsel the patient, the patient may wait on hold until a physician becomes available or disconnect from the system and try again later. The system otherwise tells the patient that no physicians are available to counsel the patient.

An available physician that accepts the patient call is immediately provided with the medical history (246) of the patient, including the current symptoms. Information may be conveyed to the physician by telephone, a secured internet interface, fax, email, etc. The physician may be given time to review the medical history (248) of the patient and to do any necessary pre-consultation research while the patient waits on hold. The system may notify the patient of the physician's activity, convey disclaimers, or convey advertisements while the patient is on hold. In one embodiment, the patient may choose to have a medical question answered by the physician via email. Here, the system tracks the emailing process and bills the patient for the medical advice. Alternatively, the patient is connected directly to the physician (250). The physician thereafter provides medical advice to the patient.

In an alternative embodiment, the physician may reroute the patient to another physician (i.e. a specialist) (254) at any point prior to or during consultation. In this case, the patient may also include a general practitioner physician seeking advice from a specialist (e.g. a dermatologist). The specialist is preferably registered with the system of the present invention to enable on-demand routing. The physician may route the patient directly to a specific specialist, the system may route the patient to a specialist according to input criteria entered by the physician, or the system may route the patient according to an algorithm that considers a variety of factors, including specialist qualifications, rates, location, availability, or any other previously described searchable qualities described herein. In a particularly preferred embodiment, routing is at least partially based on the bidding system disclosed in U.S. Pat. No. 7,076,037. In this embodiment, the system routes the patient to a specialist placing the highest bid per contact received. Once routed to a specialist (254), the patient will receive medical advice (252).

During the counseling session (252), the physician may determine the customer needs a house call and can request the appropriate assistance through the system of the present invention. Alternatively, the patient requests the house call directly through the system.

The information exchanged between the physician and the patient during the counseling session is stored in the system database and is thereafter accessible only by authorized parties. Such information may include call time, diagnosis, and recommended treatment. Optionally, the conversation is recorded. The physician may supplement a recorded conversation with file notes after the counseling session ends (256). Preferably, the physician can record/write medical notes directly to the patient file. Medical notes are posted to the patient account in real-time. Such notes may be posted to the account as an audio file or transcribed into text. An audio file may, alternatively, be automatically transmitted to a third-party transcribing service that converts the audio notes to properly formatted medical notes. Preferably, IVR transcribes the physician notes immediately following the counseling session. The patient may access the notes in the on-line account for a follow up or other consultation session with another physician.

After conclusion of the counseling session, the patient may have the opportunity to rate the physician (258) or the overall consultation experience. Ratings implement quality control mechanisms into the system. The quality control mechanisms (e.g. surveys) may be conducted over the Internet (e.g. on-line forms), via IVR, or with a live operator. The system may ask the patient specific questions regarding satisfaction with the physician. Alternatively, the patient fills out an open-ended form discussing the overall experience with the physician. After rating the physician (258), the patient may contact another physician (234) or disconnect (260) from the system by hanging up the telephone.

The present invention for a process for obtaining expert advice on-demand (100) and particularly obtaining expert medical advice (200), provides many advantages over existing systems. For example, patients using the present invention reach a physician immediately, instead of waiting for a return call. The present invention also incorporates routing mechanisms that more efficiently place patients in contact with high quality physicians. Moreover, secure storage of patient records accessible via IVR or the Internet provides worldwide real-time access to those records for both the patient and the physician. Physicians are immediately presented with patient medical history before accepting a call and can provide the medical history to any authorized person nearly instantaneously around the world, all in the context of telemedicine. Accordingly, the medical history can be easily and automatically updated by authorized parties. The incorporation of IVR further provides advantages over current systems such as convenience, speed, cost effectiveness, and less reliance on employees to run the overall system. As described above, physicians may also distribute "call me buttons" for automatically connecting to the system. That is, a patient may click on a physician "call me button" through a website to immediately connect to the physician of choice. Alternatively, the patient can schedule a counseling session with a physician when a specific physician is unavailable. The present invention also incorporates a robust feedback system, especially utilizing feedback from patients, not incorporated into other existing systems.

The process for obtaining expert medical advice (200) may also be used in conjunction with insurance companies, third party administrators (TPAs) and corporations. In this embodiment, the insurance company, TPA or corporation registers with the system of the present invention. Payments are submitted to the administrator on a "per user" basis, for each person registered by the respective entity. Employees are enrolled as patients through the corresponding insurance company, TPA or corporation. In this embodiment, the administrator may customize the system of the present invention to ensure that the specific requirements of each entity are met. Accordingly, each entity may have a special portal to access specific physicians or other benefits specific to that entity.

Figure 3:
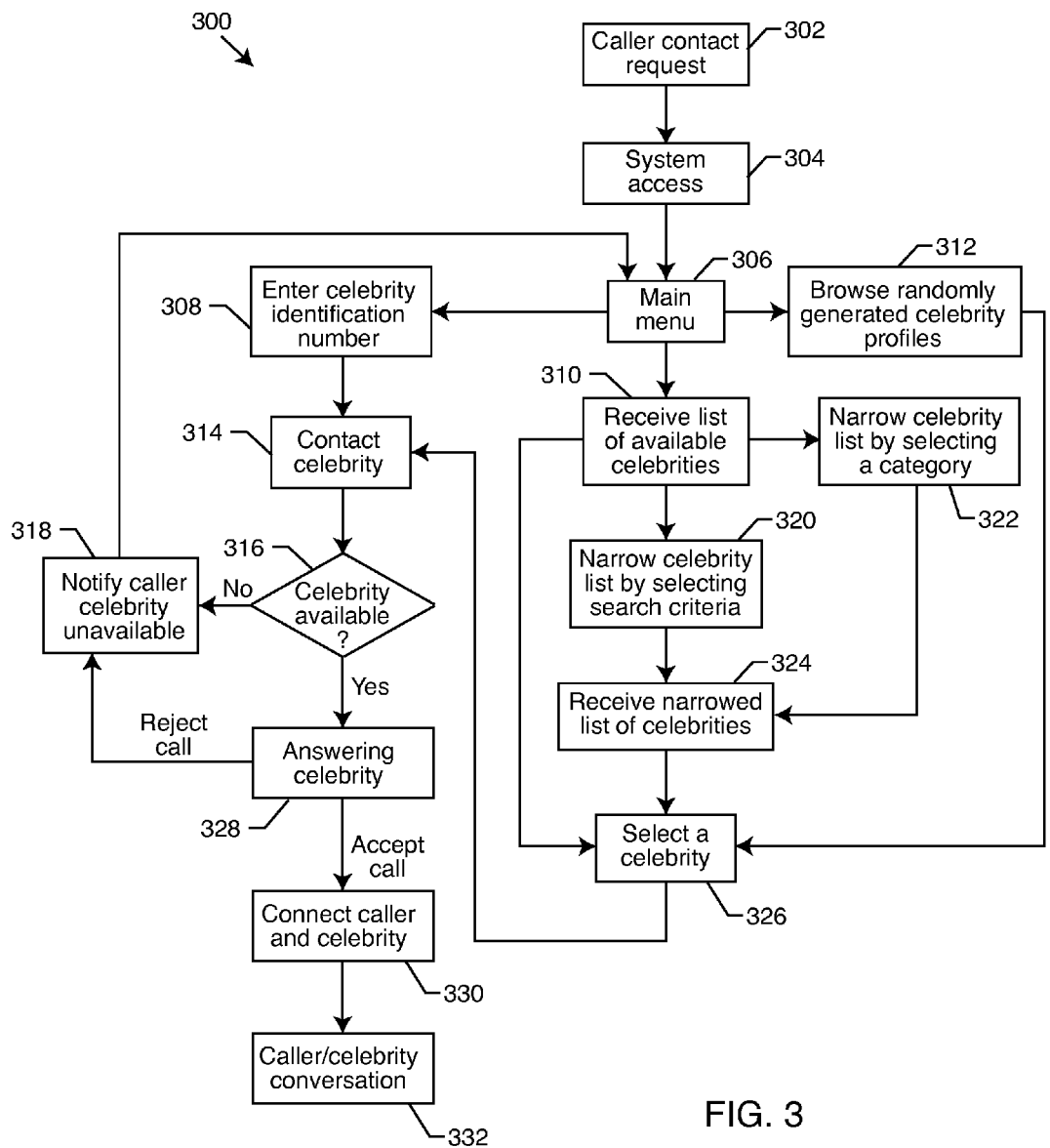
FIG. 3 is a flowchart illustrating the steps of contacting celebrities on-demand.

The system of the present invention can also be used to contact a celebrity on-demand (300), as illustrated in the flowchart in FIG. 3. Prosperity in the glamorous entertainment industry for extended time periods is extremely difficult. Consequently, many celebrities are only "famous" for a few years. Earning income may be difficult for celebrities no longer performing or starring in movies or on television. Some celebrities choose to do personal appearances for added income. Celebrities are paid to appear, autograph memorabilia, give speeches, etc. Accordingly, celebrities can earn extra income from home in accordance with the processes disclosed herein. The present invention is particularly advantageous for celebrities endeavoring to reach a worldwide fan base from the safety of a remote location.

A celebrity must first register with the system before receiving contacts from callers. Celebrity registration is similar to provider registration discussed in steps 104-114. The celebrity must enter the necessary contact information into the system. Such information may include name, address, payment terms, contacting phone number, gender, interests and detailed experiences in the entertainment industry. The celebrity may also create a profile in accordance with step 108, described above. Once the celebrity completes registration, the profile awaits administrator approval in accordance with steps 110-114. Administrator approval ensures the celebrity meets the necessary contact requirements and does not post unauthorized or inaccurate information.

A validated representative of the celebrity may, alternatively, register the celebrity with the system. Such representatives or agents may register and manage multiple celebrity accounts. In this embodiment, the representative or agent markets the name and likeness of the celebrity on behalf of the celebrity. Profits may be split among the system administrator, the celebrity and the representative or agent.

The process of contacting a celebrity on-demand (300) begins by receiving a contact request from a caller (302) via any communication network. For example, the caller may access the system (304) by dialing an access phone number. Once connected, the main menu (306) provides the caller with a set of options. In general, callers make menu selections or select celebrities by pressing buttons on a touch-tone phone or by speaking into the telephone. The system can process voice activated commands such as requesting a celebrity by name or entering a specific celebrity identification number (308). Caller selections are verified electronically by the system. Alternatively, the system may utilize an IVR based menu selection system.

As shown in FIG. 3, callers may initially have the option to enter the identification number of a specific celebrity (308); hear a list of available celebrities (310); or browse randomly generated celebrity profiles (312). The caller selects an option from the main menu (306). The system may request that the caller re-enter a valid option when an invalid menu or celebrity identity number is entered. Moreover, the system may limit the number of invalid entries before disconnecting the caller from the system altogether. Disconnecting the caller frees additional system resources for other callers. The system immediately contacts the celebrity (314) after a caller enters a valid celebrity identification number (308). When checking celebrity availability (316), the caller is notified (318) when a specific celebrity is unavailable. The caller is then directed back to the main menu (306).

Alternatively, the caller may receive a list of available celebrities in the system (310). Celebrity profiles are generally available over the phone, on the Internet, or via the IVR system. In one embodiment, the celebrity list may be narrowed by selecting search criteria (320) via a series of menus that categorize the celebrities. Celebrities and corresponding profiles are associated with searchable keywords. Callers search for celebrities based on these keywords. The keywords may associate celebrities with names, movies, directors, characters, past performances or virtually any other word associated with the name and likeness of the celebrity. Callers may also select from a list of categories (322) to narrow the celebrity list. Such categories are available through the on-line menu system. Example menu categories may include gender, television, movies, etc. Thereafter, the caller receives a narrowed list of celebrity profiles (324) from the system. The system tracks celebrity availability in real-time and preferably only provides the caller with a list of available celebrities. The celebrity profiles contain a variety of information concerning the celebrity, including biographical and performance information. Accordingly, the caller selects a celebrity (326) from the list. The celebrity is then contacted (314).

Celebrities that would otherwise be unavailable may be included on the list when capable of being alerted of caller contacts (314). For example, an alert mechanism may be integrated into the system of the present invention to notify the celebrity of a caller contact. The answering celebrity (328) receives the contact notification and may choose to accept the call remotely or reject the call. The caller and celebrity are free to converse, as described below, when the answering celebrity (328) accepts the call. The caller is otherwise informed that the celebrity is unavailable (318) when the celebrity rejects the call. Alternatively, celebrities may set available hours in lieu of the notification system.

Likewise, an available answering celebrity (328) selected by the caller may then accept the call or reject the call. The caller is notified that the celebrity is unavailable (318) when the celebrity rejects the call. The caller may then have the option to leave the celebrity a voice mail, a text message or email. Additionally, the system may allow callers to schedule calls with the celebrity when the celebrity is unavailable. When the celebrity accepts the call, the caller and celebrity are connected (330) to one another. Once connected (330), the caller and celebrity may freely converse (332). Conversations may be recorded and emailed to the caller for an additional fee.

The system may charge callers a rate fee (e.g. dollars per minute), a flat fee (e.g. a single connection fee), or combination thereof, as described above, for contacting celebrities. Preferably, callers pay a per minute rate fee set by the celebrity or the system administrator. The rate fee may alternatively be established via an auction/bidding system. For example, callers bid against one another to speak with a specific celebrity for a predetermined call length (such as five-minutes, ten-minutes, twenty-minutes, etc.). The system may set a minimum starting bid to cover contracted cost obligations to the celebrity. The celebrity can choose to receive a single call for a specified duration or multiple calls for multiple durations. Of course, the final bidded rate fee will ultimately depend on celebrity appeal and the demand to speak with that celebrity. Alternatively, the system merely charges the caller a flat connection fee for the entire conversation with the celebrity. Likewise, these calls may also have time limits governed by the system administrator.

Additionally, celebrities may sell goods and services, other than phone conversations, through the system of the present invention. Celebrities may sell photographs, ring tones, on-line chats, voice mail greetings for callers, email responses, or provide other digital downloads or merchandise known in the art. The administrator can track all non-call based purchases from celebrities. The administrator can also run promotions to grant callers "free celebrity talk time" in order to promote the system of the present invention.

The system may be designed in association with charities. Celebrities may donate all or a portion of any revenue generated through conversations with callers or the sale of goods and services. The system would automatically handle money transfer to the charity of choice. Alternatively, the system of the present invention could be licensed to the charity so the charity itself can raise the money directly.

As generally described above, callers may purchase gift cards for friends. The gift cards have minute allotments that allow non-registered callers to talk with celebrities for the duration remaining on the gift card.

In other aspects of the present invention, the system may employ an age control mechanism to ensure callers meet requisite age requirements. Underage persons or other persons unable to establish an age would be blocked from accessing the menus. Moreover, celebrities may blacklist callers, account numbers or caller telephone numbers.

Other aspects of contacting a celebrity on-demand (300) are substantially similar to processes and steps generally described above. For example, the administrator may adjust celebrity ratings or temporarily suspend and even permanently cancel celebrity accounts in according to paragraph 24, receive and administer support tickets according to paragraph 22 and monitor or approve celebrity payments according to paragraph 23. Additionally, callers may rate celebrities based on the call experience similar to step 258. Moreover, celebrities may also use "call me buttons", as described in paragraph 35, and other on-line/internet-based links to automatically connect with callers.

Although several embodiments have been described in detail for purposes of illustration, various modifications may be made to each without departing from the scope and spirit of the invention. Accordingly, the invention is not to be limited, except as by the appended claims.

What is claimed is:

1. A process for providing via telephone expert advice on-demand, comprising the steps of:

registering available medical experts in an electronic database based upon geographic location and licenses or credentials to dispense medical advice in the geographic location;

maintaining a substantially real-time list of available medical experts in medical fields, in the electronic database;

creating in the electronic database a customer account associated with a customer including a current geographic location for the customer;

permitting the customer to enter medical history information into the customer account;

storing the medical history information in the customer account;

receiving a telephone request from the customer for expert advice in one or more of the medical fields;

electronically identifying one or more available medical experts to the customer in response to the request received;

routing the telephone request for expert advice via telephone to at least one of the available medical experts based upon the geographic location of the at least one of the available medical experts and the current geographic location of the customer; and providing the available medical expert to who the telephone request was routed with the medical history information in the customer account.

2. The process of claim 1, including the step of rating the list of available medical experts, wherein the customer is routed to a highest rated available medical expert in the selected field.

3. The process of claim 2, including the step of rerouting the customer to a next highest rated medical expert when the highest rated medical expert does not respond to or rejects the request for expert advice.

4. The process of claim 2, including the step of rating the medical expert by the customer.

5. The process of claim 1, including the step of ranking the list of available medical experts from a lowest bidding available expert to a highest bidding medical expert, wherein the requestor is routed to the lowest bidding available medical expert in the medical field.

6. The process of claim 1, wherein the routing step includes the step of routing the customer to an available medical expert selected by the customer.

7. The process of claim 6, including the step of rerouting the customer via telephone to a new medical expert on the list as selected by the customer, by a computer, by the first selected medical expert, or randomly.

8. The process of claim 1, including the step of establishing a communication link between the customer and the selected medical expert.

9. The process of claim 8, including the step of connecting the medical expert to the customer over an electronic communication network.

10. The process of claim 1, including the step of associating the customer account with the customer by caller identification, Automatic Number Identification, or input data.

11. The process of claim 1, wherein the receiving step includes the step of receiving a username/password, an account number, or a voucher number from the customer.

12. The process of claim 1, including the step of assigning each of the medical experts a unique identification number or a username/password.

13. The process of claim 1, including the step of conveying an advertisement to the customer before routing the customer to the medical expert.

14. A process for providing via telephone expert advice on-demand, comprising the steps of:

registering available medical experts in an electronic database based upon geographic location and licenses or credentials to dispense medical advice in the geographic location;

maintaining a substantially real-time list of available medical experts in medical fields, in the electronic database;

creating in the electronic database a customer account associated with a customer including a current geographic location for the customer;

permitting the customer to enter medical history information into the customer account;

storing the medical history information in the customer account;

receiving a telephone request from the customer for expert advice in one or more of the medical fields;

electronically identifying one or more available medical experts to the customer in response to the request received based upon the geographic locations of the one or more available medical experts and the current geographic location of the customer;

routing the telephone request for expert advice via telephone to at least one of the available medical experts selected by the customer;

providing the selected medical expert with the medical history information in the customer account;

rerouting the customer via telephone to a new medical expert on the list as selected by the customer, by a computer, by the first selected expert, or randomly based upon the geographic location of the new medical expert and the current geographic location of the customer;

providing the new medical expert with the medical history information in the customer account; and establishing a communication link via telephone between the customer, on the one hand, and the selected medical expert or the new medical expert, on the other hand, over an electronic communication network.

15. The process of claim 14, including the step of conveying an advertisement to the customer before routing the customer to the medical expert.

16. The process of claim 14, including the steps of:

rating the list of available medical experts, wherein the customer is routed to a highest rated available medical expert in the selected medical field;

rerouting the customer via telephone to a next highest rated medical expert when the highest rated medical expert does not respond to or rejects the request for expert advice; and rating the medical expert by the customer.

17. The process of claim 14, including the step of ranking the list of available medical experts from a lowest bidding available medical expert to a highest bidding medical expert, wherein the requestor is routed to the lowest bidding available medical expert in the selected medical field.

18. The process of claim 14, including the step of: associating the customer account with the customer by caller identification, Automatic Number Identification, or input data.

* * * * *